United States Patent [19]
Glabiszewski

[11] Patent Number: 4,595,179
[45] Date of Patent: Jun. 17, 1986

[54] HYRAULIC DAMPING DEVICE AND ARTIFICIAL JOINT EMPLOYING THE DEVICE

[75] Inventor: Richard Glabiszewski, Duderstadt, Fed. Rep. of Germany

[73] Assignee: Otto Bock Orthopädische Industrie, KG, Duderstadt, Fed. Rep. of Germany

[21] Appl. No.: 504,847

[22] Filed: Jun. 17, 1983

[30] Foreign Application Priority Data

Jun. 18, 1982 [DE] Fed. Rep. of Germany ....... 3222885

[51] Int. Cl.⁴ .......................... F16F 9/10; B60G 13/00; B60G 15/00; A61F 2/72
[52] U.S. Cl. ..................................... 267/8 R; 188/274; 188/282; 188/285; 188/317; 188/322.21; 267/8 B; 267/64.28; 623/26; 623/39
[58] Field of Search .................... 267/8 R, 8 B, 64.28, 267/136; 188/274, 282, 285, 299, 316, 317, 319–320, 322.21; 3/1.2, 22, 26, 27

[56] References Cited
U.S. PATENT DOCUMENTS

| | | | |
|---|---|---|---|
| 1,700,044 | 1/1929 | Hales | 188/319 |
| 1,948,185 | 2/1934 | Padgett | 267/8 B |
| 2,213,823 | 9/1940 | Renfer | 188/281 X |
| 2,533,008 | 12/1950 | Hanson | 3/1.2 |
| 3,128,088 | 4/1964 | Paschakarnis | 267/8 R |
| 3,240,355 | 3/1966 | Karbowniczek | 267/8 R X |
| 3,316,558 | 5/1967 | Mortensen | 3/1.2 |
| 3,837,292 | 9/1974 | Wiebe | 267/8 R X |
| 4,212,087 | 7/1980 | Mortensen | 3/1.2 |
| 4,318,535 | 3/1982 | Imai | 267/8 R |

FOREIGN PATENT DOCUMENTS 821575 11/1951 Fed. Rep. of Germany ...... 188/274
1154818 11/1957 France ................................ 188/274

Primary Examiner—Ronald L. Frinks
Attorney, Agent, or Firm—Michael J. Striker

[57] ABSTRACT

A hydraulic damping unit, particularly for use in artificial joints. The unit includes a cylinder housing having a screw-in bottom part. A hollow piston is guided in the housing and has on its jacket a shoulder which delimits with corresponding flanges on the inner wall of the housing two chambers of variable volume for storing a hydraulic liquid. A hollow throttling piston is guided in the main piston and is formed with an annular recess which communicates with respective variable volume chambers via passages passing through the jacket of the main piston at both sides of the shoulder. In the range of both passages, the bottom of the recess of the throttling piston is connected to the outer surface of the latter via a sloping annular surface which, depending on the relative position of the throttling piston to the main piston, adjusts the clearance of the passages to control the resistance to flow of the hydraulic liquid. A set screw is arranged in the main piston opposite the end face of the throttling piston to adjust its axial position, and a counteracting return spring is arranged inside the throttling piston. Disclosed is also an artificial joint provided with the above hydraulic damping device. The lower part of the joint has a fork-shaped configuration, and the cylinder housing of the damping device is formed with pivot pins journalled in the opposite walls of the lower part. The main piston is linked to the upper part of the joint at a point which, in the aligned position of the upper and lower parts, is below the hinge axle of the joint.

10 Claims, 9 Drawing Figures

HYRAULIC DAMPING DEVICE AND ARTIFICIAL JOINT EMPLOYING THE DEVICE

BACKGROUND OF THE INVENTION

The present invention relates in general to hydraulic damping devices, particularly for use in damping the movements of an artificial joint. The device is of the type which includes a hydraulic cylinder and piston unit defining an annular chamber between the inner wall of the cylinder and the piston for storing a hydraulic medium. The piston is provided with an annular shoulder which divides the storing chamber into two partial chambers each communicating via damping passages at each side of the shoulder with a recess within the piston so that the hydraulic medium may pass from one partial chamber into the other and vice versa.

In prior-art damping cylinder and piston units of this kind, the partial chambers in general are arranged one after the other in axial direction. Known is also to provide two cylinder spaces of variable volume, whereby the piston during its movement reduces the volume of the first space or partial chamber and the hydraulic liquid flows through a connecting conduit in the correspondingly enlarged second partial chamber. The first partial chamber has been provided with a piston biased by a resetting element to act on the hydraulic medium.

Such prior-art hydraulic damping cylinder and piston units require relatively large installation space, and therefore are unsuitable for many applications. For example, in spite of the fact that the movements of an artificial joint can be damped with advantage by the hydraulic damping device of this kind, the practical utilization of the latter in the artificial joint encountered considerable difficulties. For example, due to the considerable length of conventional damping cylinders, the artificial knee joint has reached too far in the calf part, thus causing a very disadvantageous construction. In particular, hitherto it was impossible to construct an artificial joint in a modular form, inasmuch as the latter presumes that the knee joint does not extend to the calf part but is exchangeably mounted.

SUMMARY OF THE INVENTION

It is therefore a general object of the present invention to overcome the aforementioned disadvantages.

More particularly, it is an object of the invention to provide an improved hydraulic damping device of the aforedescribed kind which can be set up in limited space.

An additional object of the invention is to provide such an improved damping device which is particularly suitable for installation in an artificial joint in such a manner that the latter can be designed with a modular construction.

In keeping with these objects and others which will become apparent hereafter one feature of the invention in a hydraulic damping cylinder and piston unit of the aforedescribed type, resides in the provision of a throttling piston which is coaxially arranged for movement in the main piston of the unit and which is formed on its jacket with an annular recess acting as a pressure equalizing chamber which communicates via passages at each side of the shoulder on the main piston with respective partial chambers, the annular wall of the recess in the range of the connecting passages being inclined so as to adjustably throttle the cross section of the connecting passages during the movement of the throttling piston, and the throttling piston cooperating with means for adjusting its axial position relative to the connecting openings, the adjusting means being preferably in the form of a return spring acting on the throttling piston against a setting screw.

The invention thus integrates the function of the equalizing chamber with the function of the throttling piston. The length of the annular equalizing chamber is within the range of combined partial chambers of the main piston. By virtue of the annular configuration of the equalizing chamber, the hydraulic liquid stored in the partial chamber now flows along a path of reduced length and consequently the heating of the hydraulic liquid is also reduced.

Another advantageous feature of this invention is the arrangement of communication passages at both sides of the shoulder in the storing chamber. The shoulder during the movement of the main piston in one direction reduces the volume of one partial chamber while increasing the volume of the other partial chamber, thus enhancing the throughflow of the hydraulic liquid.

Another advantageous feature of this invention is the arrangement of the throttling sloping surface between the bottom of the liquid equalizing chamber and the jacket of the throttling piston. In this manner the cross section of the throughflow or connecting passages can be adjusted in very effective manner by changing the relative axial position of the throttling piston to the main piston.

The annular equalizing chamber between the inner wall of the main piston and the annular recessed part of the throttling piston, due to the variable cross section of one connecting passage, receives the incoming hydraulic fluid during the displacement of the main piston in the cylinder with an adjustable flow resistance.

Preferably, the throttling piston movable within the hollow main piston is also made hollow to accommodate a correspondingly shaped resetting element, preferably in the form of a helical spring. Due to this telescoping arrangement, a very compact and space-saving construction is obtained.

For adjusting the angular position of the throttling piston relative to the main piston, the latter, in one embodiment is formed with a threaded hole communicating with an end face of the throttling cylinder for engaging a setting screw which acts on the throttling piston against the force of the return spring. Preferably, the threaded hole is inclined relative to the axis of the main piston, and the setting screw has a conical tip engaging the end face of the throttling piston.

It is also of advantage when the outer surface portion of the cylinder opposite the storing chamber for the hydraulic liquid is formed with cooling ribs for disipating heat from the liquid in the ambient atmosphere.

In still another advantageous embodiment of this invention, the cylinder is closed at one end with a bottom part screwed into the top part to delimit the annular storing chamber. The bottom part is provided with an annular recess for receiving a sealing ring engaging the lower part of the main piston. This two-part construction facilitates the assembly or disassembly of the unit and simplifies the filling of the hydraulic liquid in the cylinder. In prior-art damping cylinders, the filling of the hydraulic liquid was a cumbersome operation, necessitating additional component parts.

According to this invention, the main piston has a length which exceeds the length of the storing chamber even if the piston is pulled out to its limit position in which the shoulder abuts against a stop surface of the cylinder, and the bottom part of the cylinder, when being only partially screwed in the upper part, does not establish a complete sealing contact with the overlapping end of the main piston. Only when the bottom part is completely screwed into the upper part, is the sealing ring brought into its full sealing position, which is then retained for any axial position of the main piston. Preferably, another sealing ring is provided in the outer wall of the bottom part at a location which establishes a full sealing contact at the moment when a corresponding full sealing contact is made between the main cylinder and the bottom part. By virtue of this arrangement, the filling operation is extremely simple. The bottom part is screwed off and removed from the top part of the cylinder, the main piston is pulled out to its limit position, and the throttling cylinder is displaced so as to open all throughflow passages. Then the hydraulic liquid is charged in the storing chamber between the main piston and the cylinder. Air cushion present in the equalizing chamber prevents any substantial leakage of the hydraulic liquid from the storing chamber into the equalizing chamber. The liquid is filled up to the level of the free end of the main piston. Thereupon, the bottom part is inserted from above in the upper part to engage its inner thread and screwed towards its end position. Initially, the inner sealing ring is not in full contact with the outer surface of the main piston and permits the outflow of excessive hydraulic liquid. Only when the bottom part approaches its end position, is the sealing ring brought into full sealing contact with the main piston, and the hydraulic liquid is compressed through a communication passage against the air cushion in the equalizing chamber. The air cushion is thus compressed when the bottom part is fully screwed in. As a consequence, in this end position of the main piston the hydraulic liquid fully occupies the main storing chamber and partially enters the annular equalizing chamber. The screwing of the bottom part into its end position thus results in a complete air discharge from one part of the storing chamber and a partial air discharge from the equalizing chamber. The dosing of the hydraulic liquid is such that the part contained in the equalizing chamber may compensate for liquid losses which during the operation of the damping device may occur in the storing chamber.

This invention also relates to an artificial joint, especially a knee joint having a hinge axle supporting an upper part of the joint for rotation relative to a lower part, whereby the aforedescribed damping cylinder and piston unit is hinged between the upper and lower parts. According to one feature of this invention, the lower part has a bifurcated configuration with bushings for pivotally supporting the cylinder of the damping device, whereas the main piston is hinged to the upper part of the joint. By disconnectably hinging the cylinder of the damping device between the prongs of the fork-shaped lower part of the joint, a relatively small and compact modular construction of the joint is achieved. The opposite ends of the joint are provided with adjustable connecting pieces for a tubular square pin part of the user.

The artificial joint according to this invention does not exceed in size the conventional artificial joints using mechanical damping. Consequently, the joint according to this invention is readily exchangeable for existing artificial joint units whereby the skeleton parts remain unchanged. The exchangeability of prior-art hydraulically damped joints was not possible because the hydraulic cylinder reached up to the calf part of the skeleton structure, and therefore the exchange could be made only by redesigning the skeleton structure.

In the preferred embodiment of this invention, the axis of the link of the damping cylinder on the upper part of the joint is below the hinge axle, so that the damping action during the angular movement of the two parts of the joint is most effective. At larger bending of the joint, the damping action of the device ceases, and consequently the bending of a knee joint, for example, can be accomplished without obstacles up to the sitting position. The artificial knee joint according to this invention makes it possible to achieve a substantially larger bending angle than conventional joints, where the link of the damping cylinder is above the hinge axle and consequently larger bending is impaired.

It is of particular advantage when the upper part of the damping device is hinged to an extension piece which projects beyond the hinge and is fixed at its free end to the upper part of the joint. In this manner, the damping device of this invention is made an integral part of the hinge of the upper part of the joint. Since only the extension projecting from the link of the damping device is connected to the upper part, a simplification of the installation of the joint is achieved, inasmuch as the entire damping device is fastened by several screws only and hence can be easily replaced when, for example, too much liquid has leaked out from the damping cylinder so that the latter does not perform its damping function properly.

The arrangement of lateral pivot pins on the damping device and the corresponding bearing bushings in the prongs of the bifurcated lower part of the joint contribute also to the ease of exchangeability. Preferably, the pivot pins are oriented against corresponding bores in the prongs of the lower part and the bearing bushings are inserted from the outside through the bores into engagement with the pin. It suffices therefore to remove only the bushings from the bores when the damping unit is to be replaced. To protect the bearing bushings from unintentional fall-out, the prongs of the yoke are provided with flat springs engaging from the outside the bearing bushings. When removing the damping cylinder, the safety springs are simply bent and the bushings are pulled out. Both the pivot pins and the bearing bushings have conically shaped bearing surfaces which provide for proper alignment of the pivot axes and in cooperation with the safety springs effectively prevent the canting of the damping device.

For protecting the damping device, it is also of advantage when the upper and lower joint parts are provided with abutment surfaces which limit the relative movement of the two joint parts before the piston of the damping device hits the wall of the cylinder. It has been found that if the step surfaces in the hydraulic cylinder are used for limiting the movement of the whole artificial joint, then the cylinder is subject to excessive loads and is prone to damage, and the overall function of the joint is impaired.

The novel features which are considered characteristic for the invention are set forth in particular in the appended claims. The invention itself, however, both as to its construction and its method of operation, together with additional objects and advantages thereof, will be best understood from the following description of specific embodiments when read in connection with the accompanying drawing.

DESCRIPTION OF THE PREFERRED EMBODIMENTS

Figure 1:
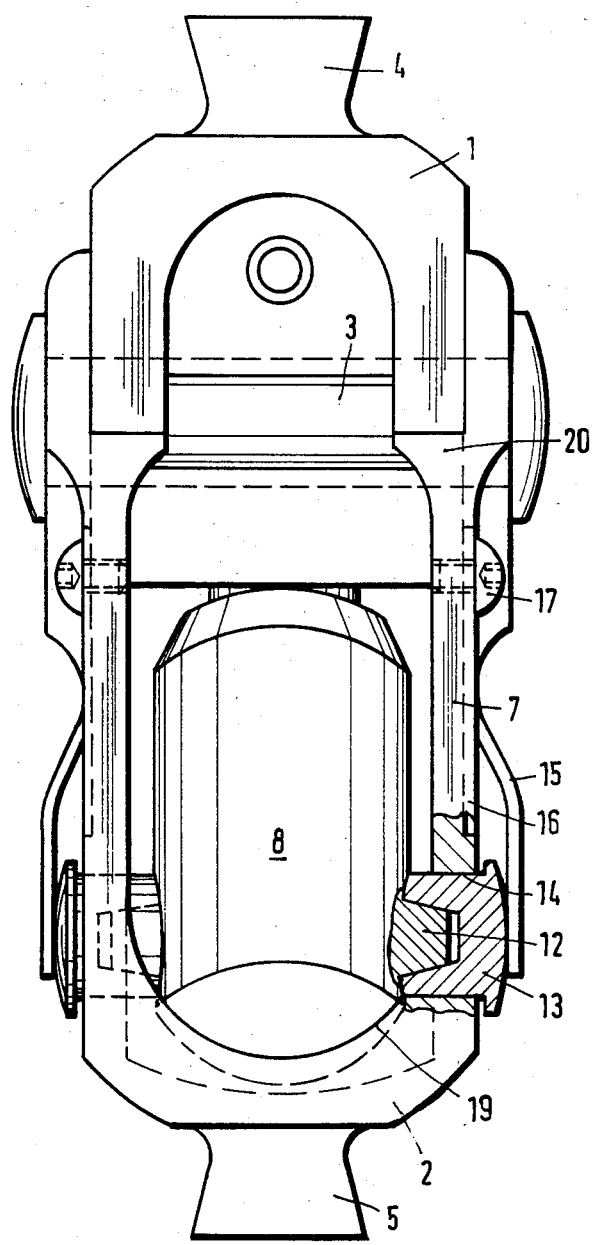
FIG. 1 is an elevational view of an artificial knee joint according to this invention in its upright position.
Figure 2:
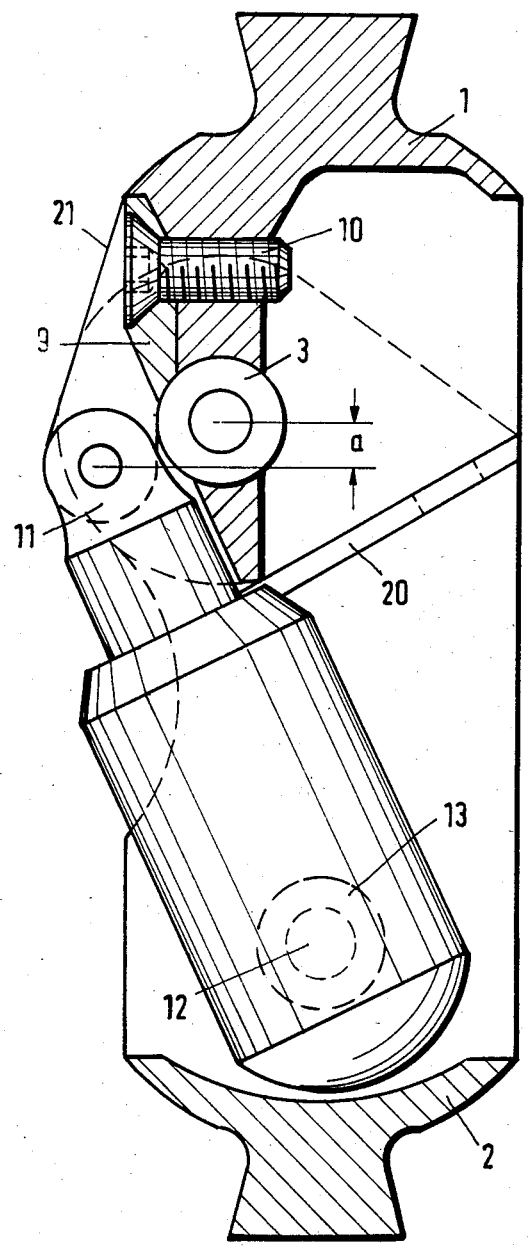
FIG. 2 is a side view, partly in section, of the knee joint of FIG. 1.
Figure 3:
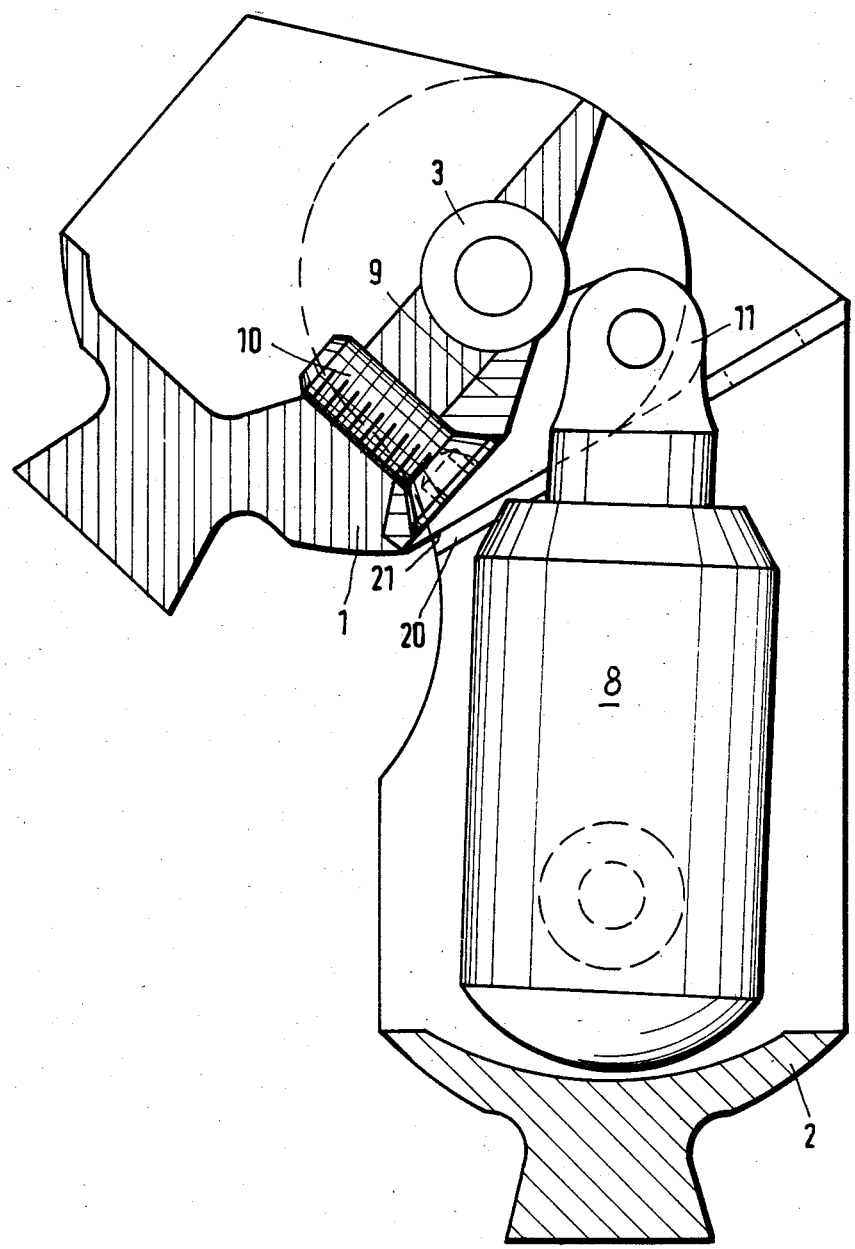
FIG. 3 is a view similar to FIG. 2 of the knee joint in its bent position.

FIGS. 1-3 show an artificial knee joint consisting of an upper part 1, a lower part 2 and a hinge axle 3 pivotably connecting the two parts one to the other.

The upper part of the joint has an adjustable connection 4 for a tubular skeleton structure on the thigh and the lower part 2 of the joint has a similar connection 5 to the tubular skeleton structure on the calf.

The lower part 2 of the joint has a bifurcated structure with two parallel walls 6 and 7 between which a hydraulic cylinder of the damping device 8 is hinged.

The piston of the hydraulic damping device is linked to an attachment 9 which is fastened to the upper part 1 by means of a screw 10. The damping device 8 is linked to the attachment 9 by means of a swivel joint 11 which presents the pivot point of the damping device on the upper part of the joint. The mounting of the damping device 8 in the lower part 2 is made by means of pivot pins 12 directed to opposite walls 6 and 7 and engaging bearing bushings 13 which in turn are inserted from the outside into bore holes 14 in respective walls 6 and 7. The pivot pins 12 as well as the bearing recesses in the bushings 13 have conical shape so that after engagement of the bushings 13 with the pivot pins 12 an automatic centering of the hydraulic damping device 8 on the lower part 2 of the knee joint takes place. The bearing bushings 13 are held in position by means of resilient yoke whose arms 15 are secured by a screw 17 to outer surfaces of respective walls 6 and 7 and are guided in recesses 16. Before insertion of the bushings 13 in the holes 14, the arms 15 of the yoke are deviated by lifting and abut resiliently against the faces of the bushings.

Both the bottom 18 of the fork-shaped lower part 2 as well as bottom 19 of the hydraulic damping device 8 are curved according to the path of the pivotal movement of the damping cylinder about the pins 12.

Both the upper part 1 and the lower part 2 are provided with abutment ledges 20 which in the upright position of the knee joint abut against each other and limit the rising movement of the artificial knee.

It will be seen particularly from FIG. 2 that in the upright condition of the knee joint the central point of the swivel joint 11 is slightly below the level of the center point of the hinge axle 3.

FIG. 3 shows the knee joint of FIG. 2 in its bent condition, that is in its sitting position. The bending movement of the artificial knee joint is limited by the abutment ledge 20 of the lower part 2, and the rear edge 21 of the upper part 1. The slope of the rear edge 21 is designed such that in the extreme bent condition of the bending joint it engages with its full length the abutment ledge 20 of the lower part 2. Due to the lower arrangement of the pivot point 11 relative to the hinge axle 3, it is possible to achieve a substantially larger bending angle of the artificial joint than in conventional constructions of the latter.

During the transition of the artificial joint from its upright position into the extreme bent position illustrated in FIG. 3, the swivel joint 11 of the hydraulic damping device 8 is moved along a circular path and to a bending angle of about 90° the hydraulic damping device is compressed. Thereafter, the damping device 8 is a little pressure released so that the force of resetting means in the damping device 8 holds the artificial joint in the bent limit position illustrated in FIG. 3. This early inactivation of the counterforce against the resetting means in the damping device 8 is the consequence of the lower arrangement of the pivot point 11 relative to the hinge axle 3.

Figure 4:
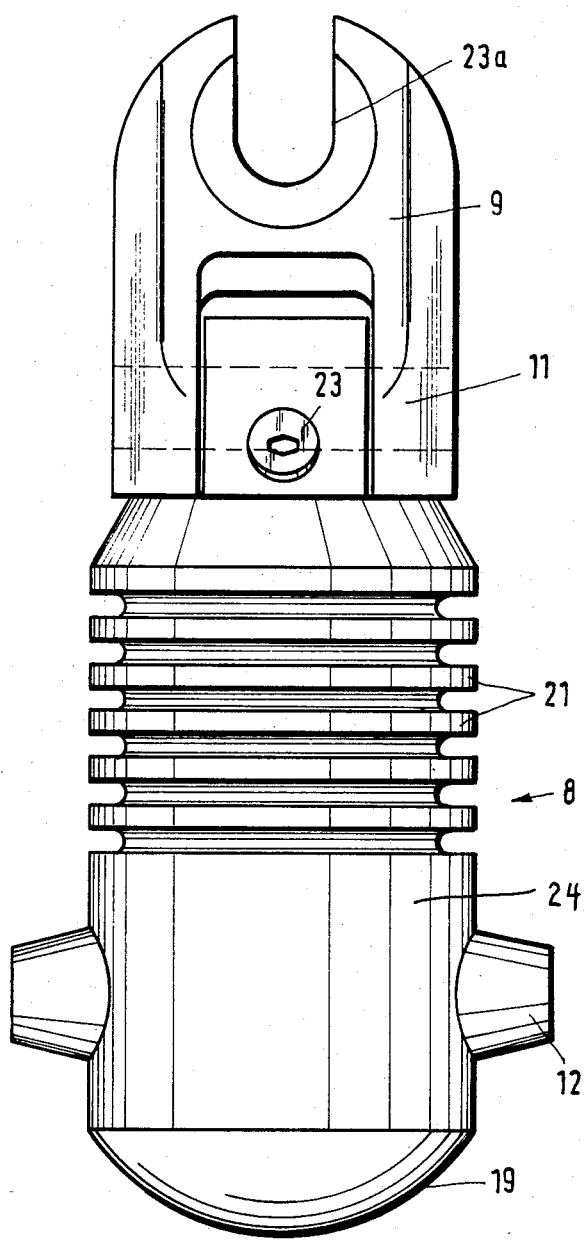
FIG. 4 is an elevational view of the hydraulic damping device shown in its retracted position and with a linking extension.

FIG. 4 illustrates an elevational view of the hydraulic damping device 8 when removed from the artificial joint. The two pivot points 12 form an integral part of the cylinder of the basic cylinder and piston unit of the device 8. The bottom part 19 of the cylinder has a convex configuration and the part of the cylinder above the pivot pins 12 is formed with cooling ribs 22 which increase the upper surface of the cylinder and improve the heat transfer from the cylinder to the outer atmosphere. The swivel joint 11 links the top of the piston of the device 8 to the attachment 9 which is provided with a recessed cut-out 23a for receiving the fastening screw 10.

Figure 5:
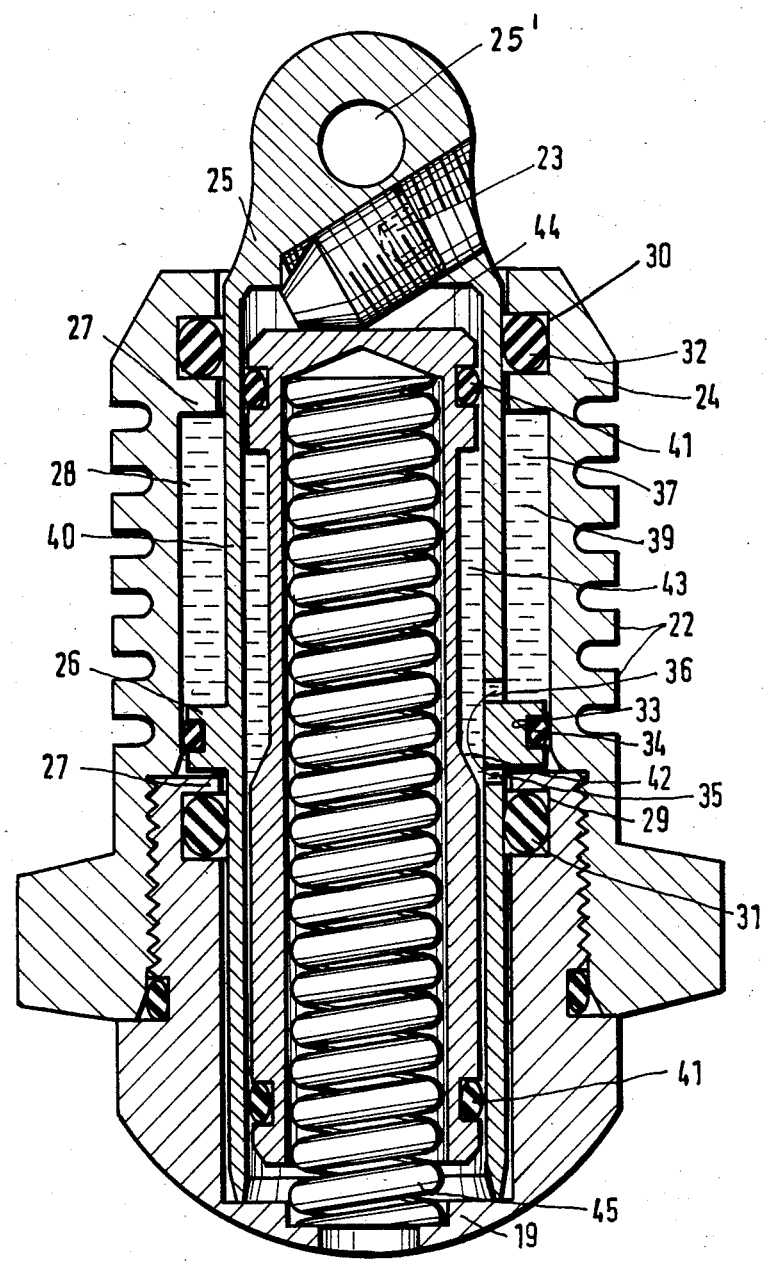
FIG. 5 is a sectional side view of the device of FIG. 4 shown without the linking extension.
Figure 6:
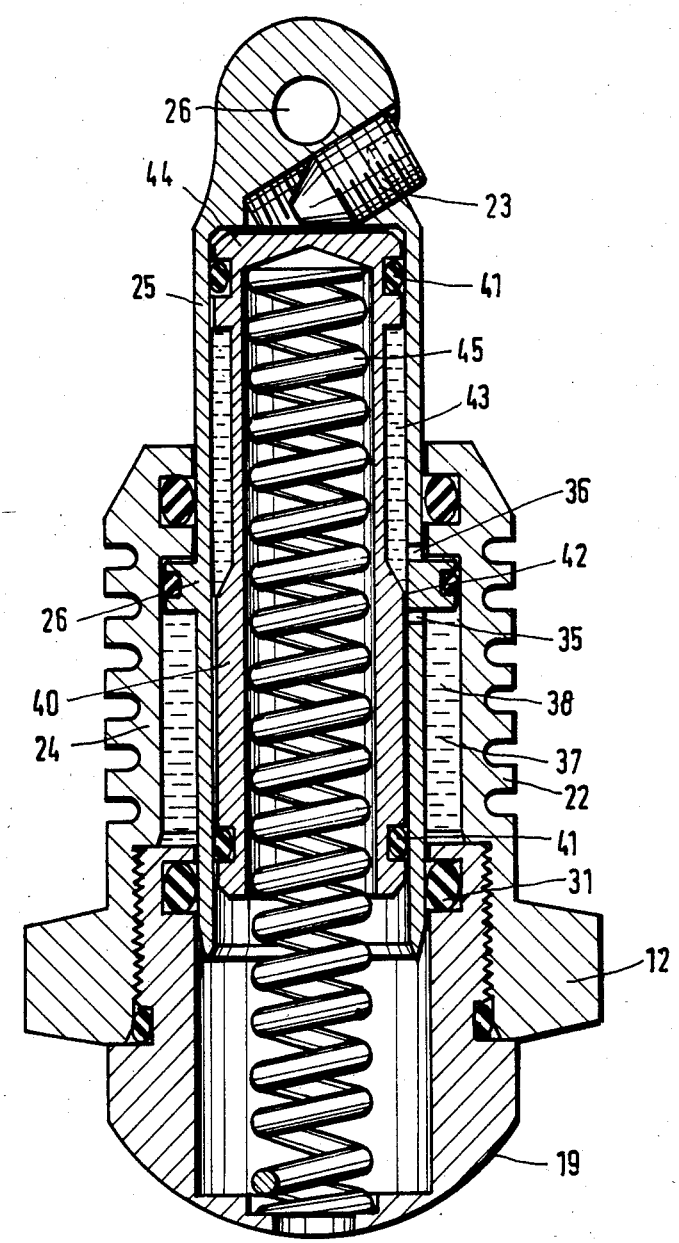
FIG. 6 is a view similar to FIG. 5 but showing the device in its extended position.

FIGS. 5 and 6 depict the inner construction of the hydraulic damping device 8. The cylindrical housing 24 is assembled of two parts screwed one to the other. The cylindrical housing guides a main piston 25 which at its free tip is formed with an eyelet 26 for receiving the pivot axle of the swivel joint 11. The main piston 25 is hollow and approximately midway of its cylindrical jacket is provided with an annular shoulder 26 projecting into an annular space 28 formed between two flanges 27 on the inner surface of the cylindrical housing 24. FIG. 5 illustrates the device with the main piston in its interposed position, whereas FIG. 6 shows the main piston in its extended position. The main piston 25 is sealed relative to the annular space 28 by means of two sealing O-rings 31 and 32 arranged in corresponding grooves 29 and 30 in the inner walls of housing 24 and its bottom part 19. The outer surface of shoulder 26 is also provided with a groove 33 for accommodating an additional sealing O-ring 34. The jacket of the main piston 25 has at both sides of the shoulder 26 through-flow passages 35 and 36 through which hydraulic fluid 37 in space 28 can flow into and out from the interior of the hollow piston 25. During the upward movement of the piston 25, the annular shoulder 26 divides the space 28 into two annular chambers of variable volume. The first variable chamber 38 is formed between the lower face of shoulder 26 and the flange 27 of the bottom part 19 of the cylinder housing 24, whereas the other variable volume chamber 39 is bounded by the opposite end face of shoulder 26 and the flange 27 at the top part of cylinder housing 24. In forcing the main piston 25 from its extended position (FIG. 6) into its interposed position (FIG. 5) the volume of the first mentioned partial chamber 38 continuously decreases while the volume of the second partial chamber 39 correspondingly increases.

In the inner space of the hollow main piston 25, there is guided for reciprocating movement a hollow throttling piston 40, which at its end portions is provided with sealing rings 41 engaging the inner wall of the hollow main piston 25. The upper half of the throttling piston 40 is provided with an annular recess 43, which in the range of passages 35 and 36 has a sloping annular wall 42 connecting the bottom of the recess 43 with the cylindrical upper surface of the lower half of the piston 40. The recessed part 43 forms an equalizing chamber for the two complementary chambers 38 and 39 in the cylinder space 28. During the displacement of the main piston 25 together with its throttling piston 40 from the extended position shown in FIG. 6 into the interposed position of FIG. 5, hydraulic liquid 37 contained in the first partial chamber 38 starts flowing through the first passage 35 in the equalizing chamber 43 and therefrom through the second throughgoing passage 36 in the second partial chamber 39. By adjusting the relative position of the throttling piston 40 in the main piston 25, the position of inclined surface 42 is changed relative to the passages 35 and 36 in the jacket of the main cylinder. In this manner the flow resistance for the hydraulic liquid during its passage from one partial chamber into the other can be selectively changed.

The adjustment of the position of the throttling piston 40 relative to the main piston 25 is effected by means of a set screw 23 which is screwed in an oblique threaded hole in the top of the main piston 25. A conically shaped tip of the set screw 23 is engageable with the end face 44 of the throttling piston 40 and acts as a limit stop for the latter. A helical return spring 45 is inserted into the interior of the hollow throttling piston 40 and exerts a counterforce against the setting force of screw 23. The resetting spring 45 is seated on the bottom part 19 of the cylinder housing 24 and engages the inner end face of the hollow throttling cylinder 40. In this manner, the helical return spring 45 urges the throttling piston 40 together with the main piston 25 from the interposed position of the latter (FIG. 5) into its extended position (FIG. 6).

It can be readily recognized that, by arranging the two partial chambers 38 and 39 in the common annular space 28 in the cylinder housing, a considerably space-saving construction is achieved. Furthermore, by designing the pistons 25 and 40 as hollow pistons, the compactness of the whole damping device is further increased, inasmuch as the return spring 45 can be coaxially arranged in the piston. Similarly, the adjustment of the damping force of the entire hydraulic damping device 8 by means of the set screw 23 and the inclined throttling wall 32 of the piston 40 is achieved without any additional space requirements.

Figure 7:
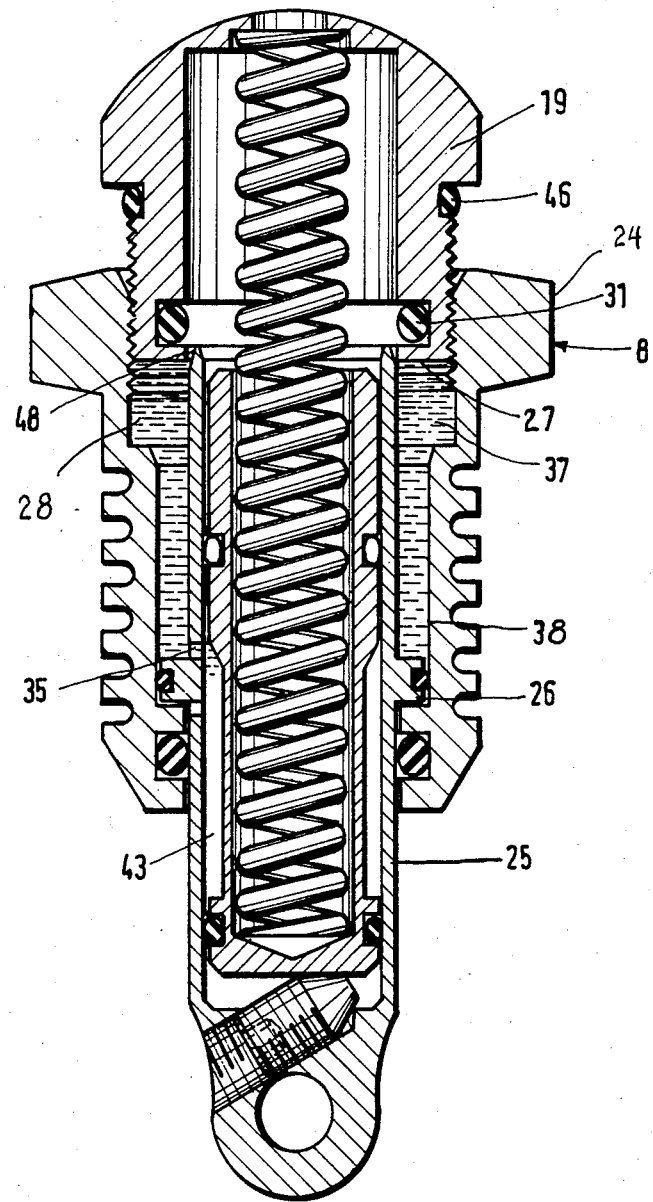
FIG. 7 is a sectional side view of the device according to FIG. 6 shown in its sealing position with partially screwed in bottom part of the cylinder.
Figure 8:
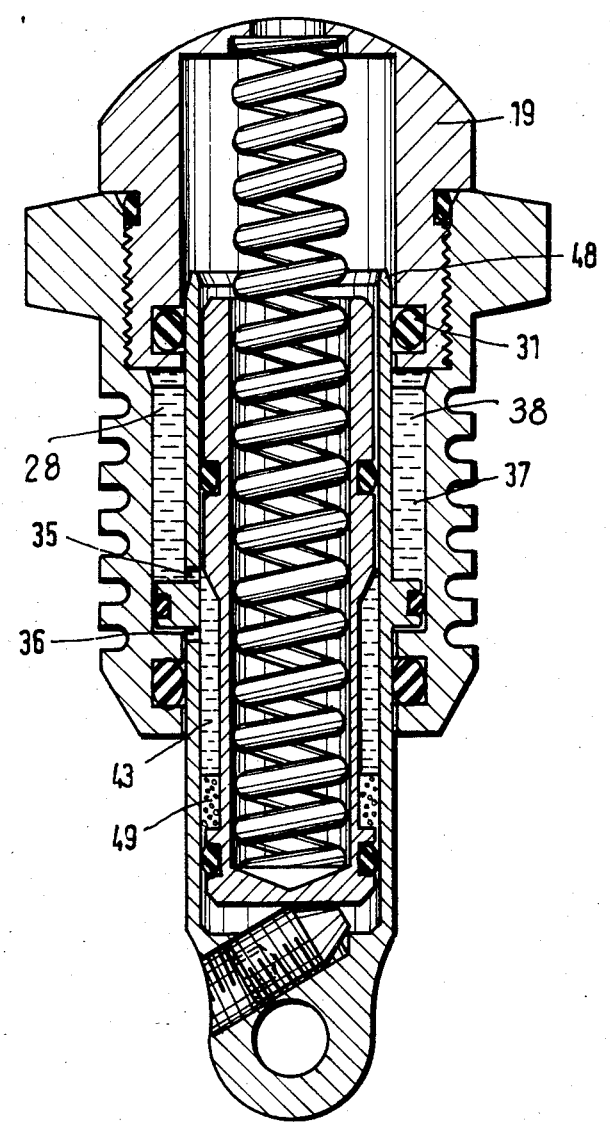
FIG. 8 is a view similar to FIG. 7 illustrating the damping device with fully screwed in bottom part of the cylinder (end of the liquid filling process)
Figure 9:
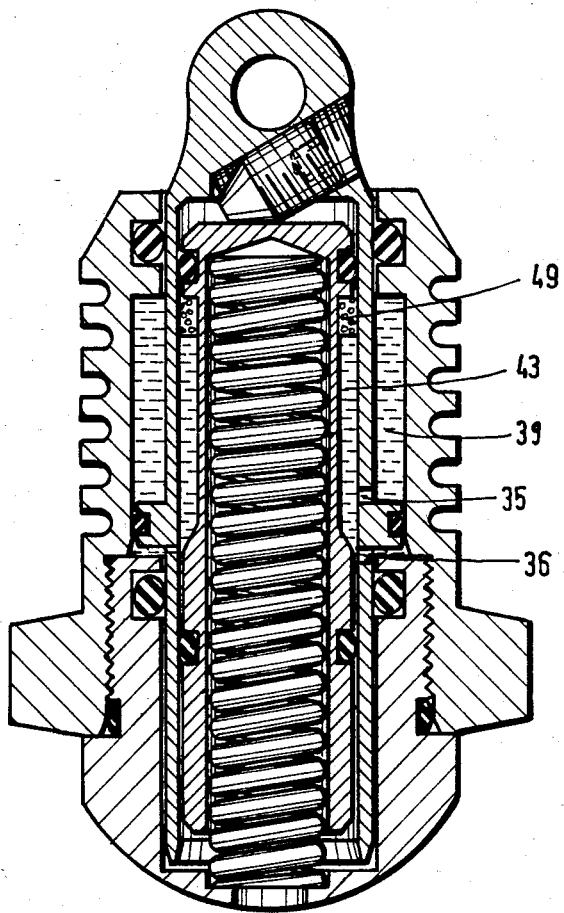
FIG. 9 shows in a sectional side view the damping device of FIG. 8 in its working position and with retracted main piston.

FIGS. 7-9 illustrate the process of filling up the hydraulic damping device according to this invention with hydraulic liquid. The cylinder housing 24 is turned upside down, that is its open end is directed upwardly, the main piston 25 is displaced into its extended position at which the annular shoulder 26 abuts against the upper flange 27 and the volume of the upper partial chamber 39 is reduced practically to zero. Thereafter the hydraulic liquid is poured into the space 28 between the main piston 25 and the inner wall of the cylindrical housing 24 which in the extended position of the main piston also includes the full volume of the partial chamber 38. The throughflow passage 35 still connects the chamber 38 with the equalizing chamber 43 in the interior of the main piston but air present in the equalizing chamber cannot escape, and therefore only a negligible amount of the hydraulic liquid penetrates into the equalizing chamber. The hydraulic liquid is filled up to the level of the rim of the open end of the main piston 25.

Then the bottom part 19 is reinserted into the open threaded end of the cylinder housing 24 and screwed down. In doing so, the annular flange 27 at the end face of the bottom part 19 presses against the surface of the hydraulic liquid 37. In this initial position, the sealing ring 31 had not yet reached the piston 25, the excess hydraulic liquid flows upwardly through the annular gap between the edge of the flange 27 and the end portion of the main piston 25. During further screwing in of the bottom part 19, the sealing ring 31 is brought into contact with the outer surface of the main piston. In order to facilitate the engagement of the sealing ring 31 with the piston, the end portion 48 of the latter is inclined inwardly. During further advance of the bottom part 19 in the cylinder housing 24, the hydraulic liquid 37 is now forced through the passage 35 in the equalizing chamber 43, whereby the air volume in the latter is compressed and forms an air cushion 49. After the bottom part 19 is completely screwed into the cylinder housing 24, the filling process is completed. The partial chamber 38 is filled up with hydraulic liquid only without the presence of air, whereas the equalizing chamber 43 is partially filled with hydraulic liquid and at its bottom and a cushion of compressed air 49 is generated.

It will be appreciated that this filling process, in comparison with filling procedures of prior-art devices of this kind, is extremely simple and ensures a trouble-free operation of the hydraulic damping device 8. It will be seen from FIG. 9 that after moving the main piston into its retracted position, the hydraulic liquid can flow through restricting passages 35 and 36 from one partial chamber 38 into the other partial chamber 39 and vice versa. The equalizing chamber 43 in the region of the passages 35 and 36 contains an air-free charge of hydraulic liquid biased by the compressed air cushion 49, so that any losses of liquid which may occur due to leakage in partial chambers 38 and 39 is readily replenished. The compressed air cushion 49 does not interfere with the operation of the device and only expands slowly when liquid from the equalizing chamber 43 is supplied in the partial chambers. The air cushion 49 thus exerts a sort of replenishing force.

It will be understood that each of the elements described above, or two or more together, may also find a useful application in other types of constructions differing from the types described above.

While the invention has been illustrated and described as embodied in a damping device for use with knee joints, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A hydraulic damping device, particularly for damping the movement of artificial joints, comprising a cylinder; a first hollow piston movable in said cylinder and having a jacket provided with an annular shoulder to define with the inner surface of the cylinder two annular chambers of variable volume for storing a hydraulic medium; a second hollow piston movable in said first hollow piston and having a jacket formed with an annular recess facing the inner wall of said first piston to act as an equalizing chamber; the jacket of said first hollow piston having at least two throughgoing passages provided at opposite sides of said shoulder to establish communication of respective variable volume chambers with the equalizing chamber; means for adjusting the cross section of at least one of said through passages, said adjusting means including a sloping wall portion arranged between said annular recess and the jacket of said second piston in the range of said two passages; and an axial position adjuster acting in one direction on said second piston and including a return member arranged in said second piston and acting thereon in opposite direction.

2. A hydraulic damping device as defined in claim 1, wherein said return member is a helical spring arranged between said cylinder and said second piston.

3. A hydraulic damping device as defined in claim 2, wherein said axial position adjuster is a set screw provided in the top part of said first piston and engageable with the end face of said second piston.

4. A hydraulic damping device as defined in claim 3, wherein the cylinder is assembled of a housing part and a bottom part screwable in an open end of the housing part.

5. A hydraulic damping device as defined in claim 4, wherein the outer surface of the housing part is provided with cooling ribs.

6. A hydraulic damping device as defined in claim 4, wherein said housing part and said bottom part are provided respectively with an annular flange each delimiting with said shoulder one of said two variable volume chambers; and said bottom and housing parts each having a sealing ring for engaging the outer surface of said first piston.

7. A hydraulic damping device as defined in claim 6, wherein the open end of said housing part is provided with an inner thread of a length sufficient for engaging said bottom part before engagement of said sealing means with the outer surface of said first piston.

8. A hydraulic damping device as defined in claim 7, wherein after fully screwing said bottom part in said housing part, the sealing means in said bottom part fully engages the outer surface of said piston even when the latter is in its extended position.

9. A hydraulic damping device as defined in claim 8, wherein the outer surface of said bottom part is provided with additional sealing means which engages the inner wall of said housing part when the bottom part is in its fully screwed in position.

10. A hydraulic damping device as defined in claim 8, wherein the open end portion of said first hollow piston has an inwardly sloping surface to guide the sealing means on said bottom part.

* * * * *